(12) United States Patent
Ohno et al.

(10) Patent No.: US 7,270,716 B2
(45) Date of Patent: Sep. 18, 2007

(54) METHOD OF SELECTING CONTACT LENS AND/OR CARE SYSTEM THEREFOR

(75) Inventors: Sadanori Ohno, Kasugai (JP); Tetsuji Kawai, Kasugai (JP); Kazuhiko Nakada, Nisshin (JP); Hiroaki Suzuki, Toki (JP)

(73) Assignee: Menicon Co., Ltd., Nagoya-Shi (JP)

( * ) Notice: Subject to any disclaimer, the term of this patent is extended or adjusted under 35 U.S.C. 154(b) by 187 days.

(21) Appl. No.: 11/223,832

(22) Filed: Sep. 9, 2005

(65) Prior Publication Data

US 2006/0003906 A1    Jan. 5, 2006

Related U.S. Application Data

(63) Continuation of application No. PCT/JP2004/001443, filed on Feb. 10, 2004.

(30) Foreign Application Priority Data

Mar. 17, 2003    (JP)    ............... 2003-072490

(51) Int. Cl.
*B08B 7/00* (2006.01)
(52) U.S. Cl. ............... 134/18; 134/42; 422/28; 422/50; 422/51; 422/68; 422/70; 422/89; 510/112
(58) Field of Classification Search ............... 134/18, 134/42; 422/28, 50, 51, 68, 70, 89; 510/112
See application file for complete search history.

(56) References Cited

U.S. PATENT DOCUMENTS

| 5,057,585 A | 10/1991 | Agou et al. |
| 5,240,735 A | 8/1993 | Lau |
| 5,460,658 A | 10/1995 | Nakagawa et al. |

OTHER PUBLICATIONS

Baguet, PhD, Joël, et al. "Normal Protein and Glycoprotein Profiles of Reflex Tears and Trace Element Composition of Basal Tears from Heavy and Slight Deposits on Soft Contact Lenses", the CLAO Journal, Apr. 1995, vol. 21, No. 2, pp. 114-121.

(Continued)

*Primary Examiner*—Zeinab EL-Arini
(74) *Attorney, Agent, or Firm*—Burr & Brown

(57) ABSTRACT

It is intended to provide a method of selecting a contact lens suitable for a wearer and/or a care system therefor, by which the occurrence of problems (for example, worsening in the feel during wearing, lowering in the oxygen permeability of the lens, shortening in the lens life, lowering in the visual acuity, corneal injury, etc.) can be minimized to thereby ensure a high safety for the eye, namely, a method which comprises collecting the lacrimal fluid of a wearer, detecting the protein content and/or the lipid content in the lacrimal fluid thus obtained (Step S5), estimating the dirt adhesion characteristics of the wearer to a contact lens based on the protein content and/or lipid content thus detected, and then selecting a contact lens suitable for the wearer and/or a care system therefor from among a plurality of contact lenses and a plurality of care systems (Step S6).

7 Claims, 2 Drawing Sheets

OTHER PUBLICATIONS

Rebeix, V., et al., "Artificial tear adsorption on soft contact lenses: methods to test surfactant efficacy", Biomaterials 21 (2000), pp. 1197-1205.

Mirejovsky, Dorla, et al., "Lipid Adsorption onto Hydrogel Contact Lens Materials. Advantages of Nile Red over Oil Red O in Visualization of Lipids", Optometry and Vision Science, American Academy of Optometry, 1991, vol. 68, No. 11, pp. 858-864.

"How Your Contact Lenses Are Selected" <URL:http://www.menicon.co.jp/first/lens.html>, retrieved online on Aug. 23, 2002.

ical tool. Thus, when a contact lens to be purchased is selected, the following examination is generally carried out:
METHOD OF SELECTING CONTACT LENS AND/OR CARE SYSTEM THEREFOR This application is a continuation of the International Application PCT/JP2004/001443, filed Feb. 10, 2004, which claims the benefit under 35 U.S.C. § 119(a)-(d) of Japanese Application 2003-072490, filed Mar. 17, 2003, the entireties of which are incorporated herein by reference.

TECHNICAL FIELD

The present invention relates to a method of selecting a contact lens and/or a care system therefor, in particular, a method of selecting, for a wearer who purchases a contact lens or exchanges contact lenses, appropriate contact lens and/or care system that do or does not adversely influence the eye of the wearer.

BACKGROUND ART

As is well known, a contact lens is a tool that is mainly used to treat a disease called "ametropia". In addition, since the contact lens requires safety, it is dealt with as a medical tool. Thus, when a contact lens to be purchased is selected, the following examination is generally carried out:

First, a purchaser (a wearer) is inquired about what kinds of eye diseases or other diseases the purchaser has suffered in the lifetime. Then, the purchaser is examined about whether the eye or eyes is or are normal, for example, the anterior eye (e.g., cornea or anterior sac) or the external eye (e.g., conjunctiva or eyelid) does not have injury or inflammation, whether the position of the crystalline lens is normal, whether the crystalline lens is not turbid, whether the eyeground is normal, whether the amount of lacrimal fluid is appropriate, and so on. In addition, in order to select a contact lens that fits the eye of the wearer and ensures a high visual acuity of the eye, a corneal curve and a visual acuity of the wearer's eye are measured to determine a base curve, a diopter, etc. of a contact lens that are suitable for the wearer's eye.

Finally, while the thus obtained examination results and a type of a contact lens (e.g., a soft, hard, or disposable contact lens) that is desired or designated by the purchaser are taken into consideration, a contact lens suitable for the wearer is selected (this method is disclosed by, e.g., the home page of Menicon Co., Ltd., see "How Your Contact Lenses Are Selected", retrieved online on Aug. 23, 2002; the Internet <URL: http://www.menicon.co.jp/first/lens.html>). When the contact lens is selected in this way, a care system therefor is additionally selected. The care system includes a lens care solution that is suitable for the material of the contact lens and can effectively remove dirt, etc. adhered to the lens so that the lens can be used in a better condition for a longer time, and additionally includes a method of caring the lens with the solution.

Meanwhile, recently, there has been proposed a contact lens that contains an organic-silicone component (a silicon-containing component) at a high proportion, for the purpose of having a sufficiently high oxygen permeability in view of safety to the eye. A Dk value (oxygen permeability coefficient) of this contact lens is effectively increased as the proportion of the organic-silicone component is increased. On the other hand, to this contact lens, a dirt component such as protein or lipid present in the lacrimal fluid of the eye easily adheres. Usually, the dirt component can be removed by an appropriately selected care system. However, in the case where this contact lens is worn by a wearer whose lacrimal fluid contains a more dirt component, the dirt component more easily adheres to the surfaces and inner portions of the lens. In this case, the dirt component cannot be sufficiently removed by a common care system. Thus, because of the adhesion and deposition of the dirt component, various problems such as worsening in the feel during wearing, lowering in the oxygen permeability of the lens, shortening in the lens life, lowering in the visual acuity, or corneal injury may occur at a high probability. That is, it is not recommended that the contact lens be worn by the wearer.

However, the conventional contact-lens selecting method is for inspecting only whether a contact lens fits the eye of a wearer or how the contact lens is felt by the wearer. Therefore, whether dirt is likely to adhere to the contact lens when the lens is worn by the wearer, that is, whether the above-described problems are likely to occur is not inspected till, after the wearer purchases and uses the lens, the purchaser feels subjective symptoms such as fogging of the lens or congestion of the eye and accordingly the lens is examined. Thus, there have been many cases where a contact lens and a care system that are not suitable for a wearer are selected.

DISCLOSURE OF THE INVENTION

The present invention has been developed in the above-explained background. It is therefore a primary object of the present invention to prevent or avoid the problem that, because of adhesion and deposition of dirt component such as protein or lipid to and on a contact lens, the eye of a wearer may suffer adverse influences such as worsening in the feel during wearing, lowering in the oxygen permeability of the lens, shortening in the lens life, lowering in the visual acuity, or corneal injury. It is a particular object of the present invention to provide a method of selecting a contact lens suitable for a wearer and/or a care system therefor, and thereby minimize the possibility of occurrence of the above-indicated problem and ensure a high safety of the eye.

The above objects have been achieved by the present invention according to which there is provided a method of selecting a contact lens and/or a care system therefor, the method being characterized by comprising (a) a step of detecting a protein content and/or a lipid content in a lacrimal fluid of a wearer who is to wear a contact lens, (b) a step of estimating, based on the detected protein content and/or lipid content, a dirt adhesion characteristic of the wearer with respect to a contact lens, and (c) a step of selecting, based on the estimated dirt adhesion characteristic, a contact lens suitable for the wearer and/or a care system therefor, from a plurality of contact lenses and a plurality of care systems.

In short, in the contact lens and/or care system selecting method in accordance with the present invention, a dirt adhesion characteristic of wearer's eye with respect to a contact lens (i.e., a degree at which dirt adheres to a contact lens because of a characteristic of the eye of each individual wearer) that has not been examined in the conventional contact-lens selecting method is examined by analyzing the protein content and/or lipid content in the lacrimal fluid of the wearer, and the thus obtained analysis results are used to select a contact lens suitable for the wearer and/or a care system therefor. Thus, before the wearer starts the use of the contact lens, it is possible to predict various problems, such as worsening in the feel during wearing, lowering in the oxygen permeability of the lens, shortening in the lens life, lowering in the visual acuity, or corneal injury, that may occur to the wearer in future. Thus, the present method can provide, for the wearer, safer contact lens and/or care system. In particular, in the case where contact lens and/or care system are or is selected for a new wearer who has no experiences of wearing a contact lens, it is very difficult to predict a dirt adhesion characteristic of the wearer's eye. However, in this case, too, the present method can be advantageously used.

According to a preferred mode of the contact lens and/or care system selecting method in accordance with the present invention, the step of detecting the protein content and/or lipid content comprises causing the lacrimal fluid to contact a coloring reagent. Since the coloring reagent is used to detect the protein and/or lipid, a very small content of the protein and/or lipid present in the lacrimal fluid can be detected as a density of a developed color (i.e., a degree of development of color). Thus, the protein content and/or the lipid content can be detected easily and cheaply.

The lacrimal fluid is preferably contacted with the coloring reagent, in (1) the method wherein the step of detecting comprises collecting, with a lacrimal-fluid collecting medium, the lacrimal fluid, and causing the thus collected lacrimal fluid to contact the coloring reagent, or (2) the method wherein the step of detecting comprises causing, in advance, a lacrimal-fluid collecting medium to contain the coloring reagent, collecting, with the lacrimal-fluid collecting medium containing the coloring reagent, the lacrimal fluid, and causing the thus collected lacrimal fluid to contact the coloring reagent contained by the lacrimal-fluid collecting medium.

According to another preferred mode of the contact lens and/or care system selecting method in accordance with the present invention, the step of detecting the protein content and/or lipid content comprises carrying out a calorimetric analysis, a spectral analysis, a fluorometric analysis, or an analysis obtained by combining two or more of those analyses. When this analysis method is employed, the protein content and/or the lipid content can be detected quickly, easily, and cheaply, without using an analysis that has conventionally been used to detect protein or lipid but takes a long detection time, requires a complicated detecting operation, or needs a high cost; such as electrophoresis, gas chromatography, liquid chromatography, thin layer chromatography, or ELISA. Thus, the contact lens suitable for the wearer and/or the care system therefor can be easily selected without putting a large economic load on the wearer or making the wearer to feel the discomfort of being examined.

Preferably, the step of detecting the protein content comprises using, as the coloring reagent, at least one reagent selected from the group consisting of Bromochlorophenol Blue, Bromophenol Blue, Bromocresol Purple, and Tetrabromophenol Blue. With this coloring reagent, the protein content can be detected more easily and sensitively.

Preferably, the step of detecting comprises using, as the lacrimal-fluid collecting medium, a thread, a paper, a tube, a polymer film, or a sponge.

BEST MODE FOR CARRYING OUT THE INVENTION

Hereinafter, there will be described in detail an embodiment of the present invention by reference to the drawings, for the purpose of elucidating the principles of the present invention.

Figure 1:
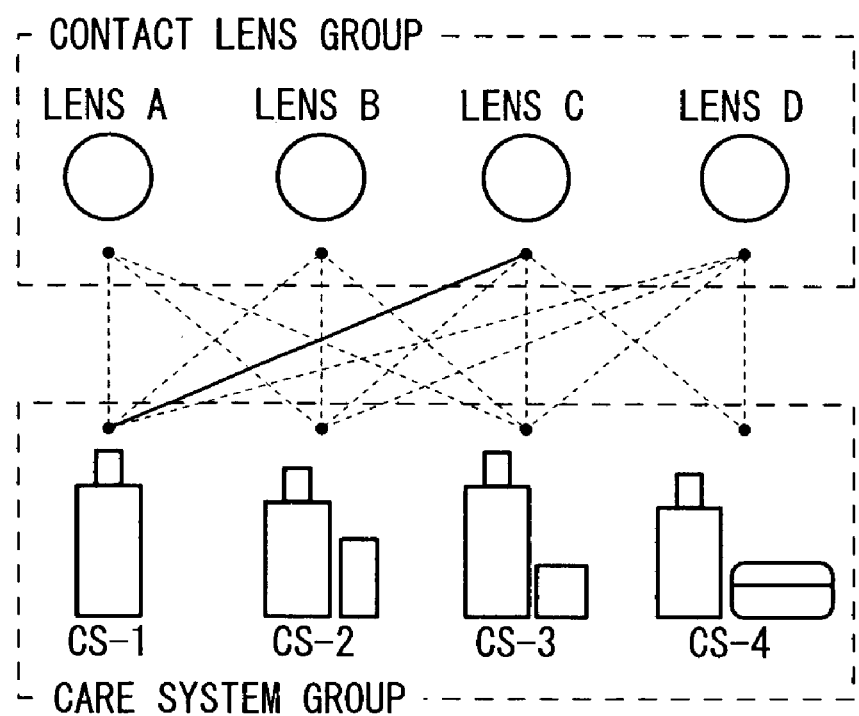
FIG. 1 is an illustrative view showing a plurality of contact lenses and a plurality of care systems that are used in an embodiment of the present invention.

FIG. 1 shows a plurality of contact lenses and a plurality of care systems that are generally kept in stock by an oculist's office, a contact-lens shop, etc. The contact lenses are classified into a plurality of sorts (i.e., lenses A, B, C, and D shown in FIG. 1), and the care systems (i.e., CS-1, CS-2, CS-3, and CS-4 shown in FIG. 1) have different cleaning effects or sterilizing effects. When a certain contact lens is selected from the plural sorts of contact lenses, a care system is selected from the plural care systems, so as to be used to care the selected lens. Contact lenses may be classified by commercial products. Since, however, respective materials of contact lenses largely influence respective degrees to which the lenses become dirty, it is preferred that the lenses be classified by at least their materials. Thus, four contact lenses A, B, C, D shown in FIG. 1 are classified by their materials. In addition, in the present invention, a care system may include not only a lens care product such as a lens care solution or tablet, or a boiling water sterilizer, but also a proposal of a method of using the lens care product. In FIG. 1 in which no using-method proposals are shown, care system CS-1 is constituted by a single solution that can clean, rinse, sterilize, and preserve a contact lens; care system CS-2 is constituted by a combination of a single solution that can clean, rinse, sterilize, and preserve a contact lens, and a protein removing solution; care system CS-3 is constituted by a combination of a solution and a tablet; and care system CS-4 is constituted by a combination of a solution and a boiling water sterilizer.

From the contact-lens group consisting of the above-described plural sorts of contact lenses and the care-system group consisting of the above-described plural sorts of care systems, appropriate contact lens and care system are selected. In the present embodiment, before the selection, first, an appropriate examination is carried out, and then a contact lens suitable for a wearer or a purchaser and a care system for the lens are selected based on the results of the examination. This is a characteristic feature of the present embodiment.

More specifically described, before a contact lens and a care system are selected, components (hereinafter, referred to as the "dirt components") that are contained by a lacrimal fluid of the wearer and may adhere to the lens are detected, and a dirt adhesion characteristic of an eye of the wearer with respect to the lens is estimated based on amounts of the detected dirt components. First, from the eye of the wearer, the lacrimal fluid is collected using an appropriate lacrimal-fluid collecting medium. The lacrimal-fluid collecting medium may be a thread such as a product commercially available under the name "ZONE-QUICK" from Menicon Co., Ltd.; a paper such as a Schirmer's test paper; a tube such as a capillary tube; a polymer film; or a sponge. However, in the present invention, the lacrimal-fluid collecting medium is not limited to the above-indicated ones so long as it can collect lacrimal fluid.

Subsequently, the thus collected lacrimal fluid is analyzed by a known method to detect contents of the dirt components present in the lacrimal fluid. The dirt components may be protein and/or lipid that are known as components that may cause worsening in the feel during wearing, lowering in the oxygen permeability of the lens, shortening in the lens life, lowering in the visual acuity, corneal injury of the eye, etc. Though a content of the protein, a content of the lipid, or a content of the sum of protein and lipid may be detected, it is preferred that both the protein content and the lipid content be detected.

The contents of the dirt components of the lacrimal fluid may be detected by the following, detecting or analyzing methods: The content of the protein may be detected by any known method such as electrophoresis, liquid chromatography, or ELISA, and likewise the content of the lipid may be detected by any known method such as gas chromatography, liquid chromatography, or thin layer chromatography. However, in the present invention, a method in which the lacrimal fluid is caused to contact coloring reagents and respective amounts of the dirt components are detected based on respective degrees of development of the colors is preferably employed because this method is easy and cheap. The degrees of development of the colors can be detected by a calorimetric analysis, a spectral analysis, a fluorometric analysis, or an analysis obtained by combining two or more of those analyses, i.e., can be detected by visual observation, a spectrophotometer, a fluorometer, etc.

In the above-described case where the method in which the lacrimal fluid is caused to contact the coloring reagents to detect the respective amounts of the dirt components is employed, the lacrimal fluid may be caused to contact the coloring reagents after the fluid is collected with the lacrimal-fluid collecting medium. However, the lacrimal fluid may be caused to contact the coloring reagents simultaneously when the lacrimal fluid is collected with the lacrimal-fluid collecting medium. In the latter case, the lacrimal-fluid collecting medium is caused to contain, in advance, the coloring reagents, and then is used to collect the lacrimal fluid (see, e.g., JP-A-4(1992)-170932.

The coloring reagents that can be used to detect the dirt components are not limited, that is, any of conventional coloring reagents that have been used to detect dirt components can be employed. However, it is preferred to employ coloring reagents that can selectively detect protein or lipid. For example, it is possible to employ Nile Blue sulfate proposed by JP-A-58(1983)-222154, erythrosine disclosed by JP-A-58(1983)-222155, non-basic dyes or basic dyes proposed by JP-A-2000-65840, dyes disclosed by JP-A-2001-166270, or triphenylmethane dyes proposed by JP-A-11(1999)-304803. Above all, when the protein is detected, it is preferred to employ at least one of the following triphenylmethane dyes: Bromochlorophenol Blue, Bromophenol Blue, Bromocresol Purple, and Tetrabromophenol Blue.

Meanwhile, the lipid can be detected by a different method than the above-described method in which the coloring reagent is used. For example, it is possible to employ (1) an enzymic method in which cholesterol esterase, peroxidase, 4-aminoantipyrine, phenol (or p-chlorophenol), and cholesterol oxidase are used, (2) an enzymic method in which cholesterol esterase, peroxidase, 4-aminoantipyrine, 3,5-dimethoxy-N-ethyl-N-(2-hydroxy-3-sulfopropyl)-aniline sodium, cholesterol oxidase, and ascorbate oxidase are used, (3) an enzymic method in which phospholipase D, choline oxidase, peroxidase, 4-aminoantipyrine, ascorbate oxidase, and 3,5-dimethoxy-N-ethyl-N-(2-hydroxy-3-sulfopropyl)-aniline sodium are used, or (4) a colorimetic method in which o-phthalaldehyde acetic acid solution and sulfuric acid are used. For example, when the above-indicated enzymic method (1) is employed, a measuring kit, "Cholesterol C—Test Wako", commercially available from Wako Pure Chemical Industries, Ltd., Japan, is advantageously used.

After the content(s) of protein and/or lipid in the lacrimal fluid is or are detected by any of the above-described detecting methods (the analyzing methods) or other known analyzing methods, the detected content(s) is or are used to estimate a dirt adhesion characteristic of the eye of the wearer with respect to the contact lens, as will be described later. The detected content(s) may be indicated by digits. Otherwise, the content(s) may be indicated by a color density or tone, so long as amounts of the dirt components can be recognized.

Based on the thus estimated dirt adhesion characteristic, a contact lens suitable for the wearer who has undergone the above-indicated examination, and/or a care system for the lens are selected from the contact-lens group and the care-system group shown in FIG. 1. That is, the contact lens and/or the care system are selected which can be estimated to be free of the problem of dirt adhesion or deposition and therefore such problems as worsening in the feel during wearing, lowering in the oxygen permeability of the lens, shortening in the lens life, lowering in the visual acuity, or corneal injury.

Since the suitable contact lens and/or care system are or is selected, the wearer (the purchaser) can obtain a safer contact lens. In the case where before the suitable contact lens and/or care system are or is selected, the wearer has designated (desired) specific contact lens and/or care system, the contact lens and/or care system designated by the wearer can be checked against, or compared with, the selected contact lens and/or care system, so as to make a judgment (i.e., a judgment of suitability) whether the designated contact lens and/or care system are or is suitable for the wearer.

Meanwhile, when the wearer's dirt adhesion characteristic with respect to the contact lens is estimated based on the protein content and/or lipid content of the lacrimal fluid and the combination of the contact lens suitable for the wearer and the care system therefor is selected based on the estimated dirt adhesion characteristic, it is desirable to determine, beforehand, appropriate criteria. With those criteria, the estimation of dirt adhesion characteristics with respect to contact lenses and the univocal and objective selection can be advantageously achieved.

The above-indicated criteria can be advantageously determined by, e.g., the following method:

<1. Method of Determining Criteria Based on Dirt Adhesion Amounts and Clinical Examination Results>

First, one contact lens is selected from a plurality of sorts of contact lenses and one care system is selected from a plurality of sorts of care systems, and the selected contact lens and the selected care system are combined. For example, in the example shown in FIG. 1, contact lens C is selected from the contact-lens group, and care system CS-1 is selected from the care-system group.

Second, a wearing test in which a plurality of arbitrary subjects ($Y_1, \ldots, Y_n$) wear contact lens C, and care lens C with care system CS-1, for a predetermined period (12 weeks) is carried out. After the wearing test, respective amounts ($P^{12}_1, \ldots, P^{12}_n$) of the protein dirt adhered and deposited to and on respective lenses C in the subjects, and respective amounts ($L^{12}_1, \ldots, L^{12}_n$) of the lipid dirt adhered and deposited to and on respective lenses C in the subjects are detected. Here, it is noted that top suffix "12" of each symbol "P" or "L" indicates 12 weeks as the wearing period; and bottom suffixes "1", . . . , "n" of symbol "P" or "L" indicate respective identification numbers of the subjects.

An amount of dirt adhered to a contact lens may be detected or analyzed by any method. For example, the dirt adhesion amount may be measured by an indirect method in which the dirt adhered to the lens is extracted using an appropriate extracting solution and an amount of the dirt contained by the thus obtained extracting solution is measured. Alternatively, the dirt adhesion amount may be measured by a direct method in which the lens to which the dirt is adhered is imaged by, e.g., a CCD camera and an amount of the dirt is measured based on the thus obtained image (see, e.g., JP-A-2002-116150).

Figure 2:
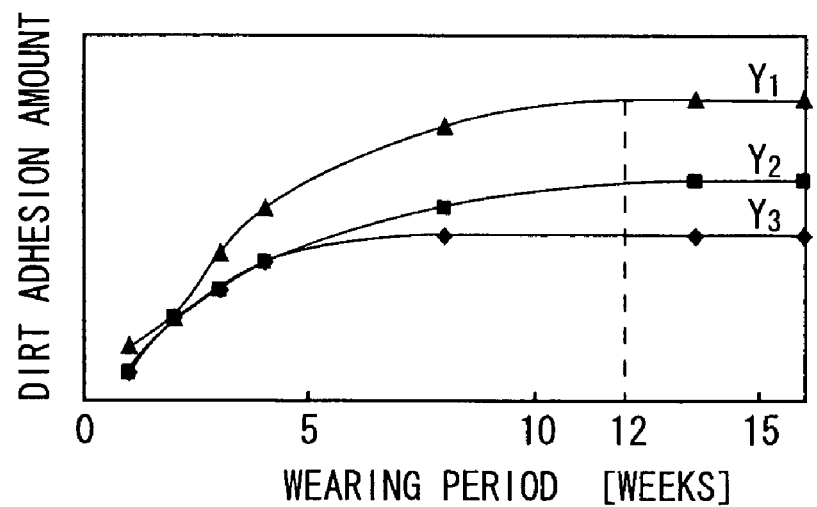
FIG. 2 is a graph representing a relationship between wearing periods and adhered dirt amounts that is obtained in a wearing test in which a contact lens C and a care system CS-1 are used.

Though the combination of contact lens C and care system CS-1 was tested for 12 weeks, an appropriate test period, i.e., an appropriate wearing period may be selected depending upon the sort of the contact lens tested. For example, since a disposable contact lens is allowed to be used for only a prescribed period (a limited period), e.g., one week, it is not appropriate to continue a wearing test for more than the prescribed period. Therefore, for example, the prescribed period (the limited period) is advantageously employed as the test period. On the other hand, since a conventional contact lens is used for a very long time, e.g., two or three years, it is difficult to employ the long period as the test period. Therefore, in the latter case, a period that is long enough for subject's dirt adhesion amounts to become substantially constant is advantageously employed as the test period. For example, FIG. 2 shows a graph representing a relationship between amount of dirt adhered and deposited to and on contact lens C and wearing period, that is obtained from each of subjects ($Y_1$, $Y_2$, $Y_3$) who underwent the wearing test using the combination of contact lens C and care system CS-1. From the graph, it can be understood that all those subjects show that the amount of dirt adhered and deposited to and on contact lens C becomes substantially constant at about 12 weeks. Therefore, it is speculated that even if the wearing test may be continued for more than 12 weeks, no significant changes would occur. Thus, for the combination of contact lens C and care system CS-1, the period of 12 weeks is selected as the test period.

After the above-described wearing test, clinical examinations are additionally carried out with respect to the eye of each subject ($Y_1$, . . . , $Y_n$), so as to evaluate the same. This evaluation is carried out by making a score for each subject according to, e.g., evaluation criteria shown in TABLE 1. In the present embodiment, the clinical examinations include a subjective examination and an objective examination. In the subjective examination, each subject evaluates his or her own feeling of wearing of contact lens C, and his or her own feeling of drying of the eye; and in the objective examination, another person such as an oculist evaluates drying, congestion, cornea stain (eye stain using, e.g., fluorescein), etc. of the eye of each subject.

TABLE 1

|  |  |  | SCORE | | | |
| --- | --- | --- | --- | --- | --- | --- |
|  |  |  | 1 | 2 | 3 | 4 |
| EVALUATION ITEMS | SUBJECTIVE EXAMINATION | FEELING OF WEARING | GOOD | NEARLY GOOD | SOMEWHAT POOR | POOR |
|  |  | FEELING OF DRYING | GOOD | NEARLY GOOD | SOMEWHAT POOR | POOR |
|  | OBJECTIVE EXAMINATION | DRYING | GOOD | NEARLY GOOD | SOMEWHAT POOR | POOR |
|  |  | CONGESTION | ABSENT | NEARLY ABSENT | SOMEWHAT PRESENT | PRESENT |
|  |  | CORNEA STAIN | ABSENT | NEARLY ABSENT | SOMEWHAT PRESENT | PRESENT |

Based on the thus obtained results of the clinical examinations, a distribution of the respective detected amounts ($P^{12}_1$, . . . , $P^{12}_n$) of adhered protein dirt of subjects ($Y_1$, . . . , $Y_n$) and a distribution of the respective detected amounts ($L^{12}_1$, . . . , $L^{12}_n$) of adhered lipid dirt of the subjects are divided into a plurality of grades, whereby a degree of suitability of the combination of contact lens C and care system CS-1 is evaluated as one of those grades.

The distribution of the amounts of adhered protein dirt and the distribution of the amounts of adhered lipid dirt are divided into the plurality of grades by, e.g., the following method: First, the obtained results of the clinical examinations are divided into four groups according to evaluation criteria shown in TABLE 2. More specifically described, the detected amounts ($P^{12}_1$, . . . , $P^{12}_n$) of adhered protein dirt and the detected amounts ($L^{12}_1$, . . . , $L^{12}_n$) of adhered lipid dirt are plotted, as shown in FIG. 3, such that the protein adhesion amount and lipid adhesion amount of each subject (subject $Y_1$ ($L^{12}_1$, $P^{12}_1$), subject $Y_2$ ($L^{12}_2$, $P^{12}_2$), . . .) is indicated by symbol "◇" if the each subject has no individual scores of 3 or 4, and has a total score of from 6 to 9; indicated by symbol "■" if the each subject has at least one individual score of 3, or has a total score of not less than 10; or indicated by symbol "×" if the each subject has at least one individual score of 4 (See FIG. 3).

Figure 3:
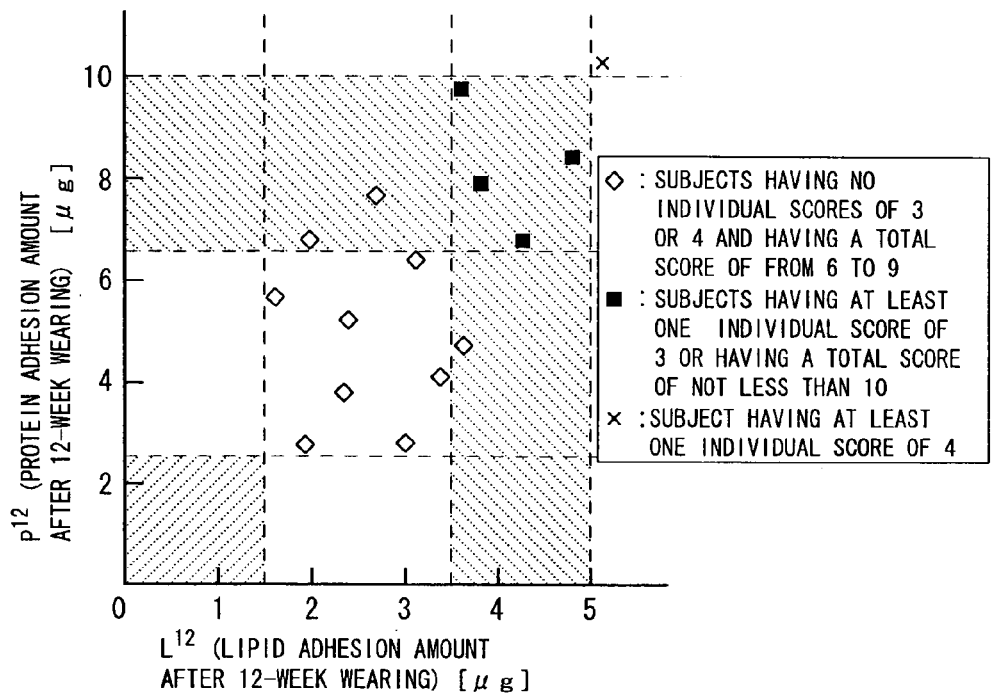
FIG. 3 is a graph representing a relationship between adhered lipid dirt amounts and adhered protein dirt amounts that is obtained in the wearing test in which the contact lens C and the care system CS-1 are used.

Next, based on the graph of FIG. 3 in which the respective dirt adhesion amounts of subjects ($Y_1$, . . . , $Y_n$) are plotted, the distribution of the amounts ($P^{12}_1$, . . . , $P^{12}_n$) of adhered protein dirt and the distribution of the amounts ($L^{12}_1$, . . . , $L^{12}_n$) of adhered lipid dirt are each divided, as shown in FIG. 3 and TABLE 3, into four grades defined by three threshold values that are equal to (1) the minimum amount of the dirt adhesion amounts indicated by symbol "×", or a smaller amount than the minimum amount, (2) the minimum amount of the dirt adhesion amounts indicated by symbol "■", or a smaller amount than the minimum amount, and (3) the minimum amount of the dirt adhesion amounts indicated by symbol "◇", or a smaller amount than the minimum amount, respectively. In TABLE 3, respective degrees of suitability of the combination of contact lens C and care system CS-1 with respect to sixteen areas in total that are defined by the four grades of protein adhesion amount and the four grades of lipid adhesion amount, are grouped into four grades, i.e., (1) a first grade, indicated by symbol "⊙", that means that wearing is fully suitable, (2) a second grade, indicated by symbol "○", that means that wearing is suitable, (3) a third grade, indicated by symbol "▲", that means that wearing needs care, and (4) a fourth grade, indicated by symbol "●", that means that wearing is not recommended.

TABLE 2

| EVALUATION CRITERIA | SYMBOLS SHOWN IN FIG. 3 |
|---|---|
| SUBJECT(S) HAVING NO INDIVIDUAL SCORES OF 3 OR 4 AND A TOTAL SCORE OF FROM 6 TO 9 | ◇ |
| SUBJECT(S) HAVING AT LEAST ONE INDIVIDUAL SCORE OF 3 OR A TOTAL SCORE OF NOT LESS THAN 10 | ■ |
| SUBJECT(S) HAVING AT LEAST ONE INDIVIDUAL SCORE OF 4 | X |

TABLE 3

| | | $L^{12}$ [μg] | | | |
|---|---|---|---|---|---|
| | | 0~1.5 | 1.5~3.5 | 3.5~5.0 | >5 |
| $P^{12}$ | 0~25 | ⊙ | ○ | ▲ | ● |
| [μg] | 2.5~6.5 | ○ | ○ | ▲ | ● |
| | 6.5~10 | ▲ | ▲ | ▲ | ● |
| | >10 | ● | ● | ● | ● |

⊙: WEARING IS FULLY GOOD
○: WEARING IS GOOD
▲: WEARING NEEDS CARE
●: WEARING IS NOT RECOMMENDED

However, it is difficult to use the thus grouped degrees of suitability of the combination of contact lens C and care system CS-1, shown in TABLE 3, as they are, to obtain criteria for estimating a dirt adhesion characteristic with respect to contact lens C, or selecting a contact lens and/or a care system according to the present invention. Hence, a relationship between dirt adhesion amounts $[(P^{12}_1, L^{12}_1), \ldots, (P^{12}_n, L^{12}_n)]$ with respect to the combination of contact lens C and care system. CS-1 and respective contents of protein and lipid in lacrimal fluid, is obtained. To this end, in addition to the above-described wearing test (the examination in which contact lens C and care system CS-1 are used), the above-described lacrimal-fluid analysis is carried out on each subject $(Y_1, \ldots, Y_n)$ so as to detect respective amounts $[(P^0_1, L^0_1), \ldots, (P^0_n, L^0_n)]$ of protein and lipid contained in the lacrimal fluid of the each subject.

TABLE 4 shows the results of the wearing test and the results of the lacrimal-fluid analysis that were obtained from each subject. From the thus obtained results, a correlation between the dirt adhesion amounts $(P^{12}, L^{12})$ obtained in the wearing test and the respective contents $(P^0, L^0)$ of protein and lipid obtained in the lacrimal-fluid analysis is determined by any of conventionally known analyzing methods such as least square method, multianalysis, or multivariate analysis. In the present embodiment, the least square method is employed to determine respective correlations for the two dirt components. The following Expressions 1 and 2 represent the correlation for the protein and the correlation for the lipid, respectively:

$$P^0 = 1.06 \times P^{12} + 1.40 \quad \text{(Expression 1)}$$

$$L^0 = 0.172 \times L^{12} + 0.032 \quad \text{(Expression 2)}$$

If the respective correlations between the dirt adhesion amounts $(P^{12}, L^{12})$ obtained in the wearing test and the respective contents $(P^0, L^0)$ of protein and lipid obtained in the lacrimal-fluid analysis are determined in this way, then it is possible to estimate, from the respective contents $(P^0, L^0)$ of protein and lipid obtained in the lacrimal-fluid analysis, dirt amounts that would be adhered to contact lens C if a wearer would use contact lens C and care system CS-1, i.e., a dirt adhesion characteristic of the wearer with respect to lens C, even if the wearer may not actually undergo the wearing test using the combination of contact lens C and care system CS-1. In addition, it is possible to determine univocally, from the estimated dirt adhesion characteristic, a degree of suitability of contact lens C for the wearer. In the present embodiment, the above-indicated Expressions 1 and 2 are used to convert TABLE 3 (grade table) into TABLE 5, by converting the dirt adhesion amounts $(P^{12}, L^{12})$ obtained in the wearing test into the respective contents $(P^0, L^0)$ of protein and lipid obtained in the lacrimal-fluid analysis.

TABLE 5

| | | $L^0$ [μg] | | | |
|---|---|---|---|---|---|
| | | 0~0.290 | 0.290~0.634 | 0.634~0.892 | >0.892 |
| $P^0$ | 0~4.05 | ⊙ | ○ | ▲ | ● |
| [μg] | 4.05~8.29 | ○ | ○ | ▲ | ● |
| | 8.29~12.0 | ▲ | ▲ | ▲ | ● |
| | >12.0 | ● | ● | ● | ● |

⊙: WEARING IS FULLY GOOD
○: WEARING IS GOOD
▲: WEARING NEEDS CARE
●: WEARING IS NOT RECOMMENDED

TABLE 4

| SUBJECTS | LACRIMAL-FLUID ANALYSIS | | WEARING TEST | | CLINICAL EXAMINATION | SUITABILITY |
|---|---|---|---|---|---|---|
| | $P^0$ [μg] | $L^0$ [μg] | $P^{12}$ [μg] | $L^{12}$ [μg] | | |
| $Y_1$ | 10.5 | 0.88 | 8.7 | 4.5 | ■ | ▲ |
| $Y_2$ | 7.8 | 0.62 | 5.9 | 3.2 | ◇ | ○ |
| $Y_3$ | 5.9 | 0.50 | 4.1 | 2.4 | ◇ | ○ |
| . | . | . | . | . | . | . |
| . | . | . | . | . | . | . |
| . | . | . | . | . | . | . |
| $Y_n$ | 6.0 | 0.67 | 4.7 | 3.6 | ◇ | ▲ |

P: PROTEIN ADHESIVE AMOUNT
L: LIPID ADHESIVE AMOUNT

Thus, the grade table (TABLE 5) indicates a grade corresponding to respective contents ($P^0$, $L^0$) of protein and lipid obtained in a lacrimal-fluid analysis. Therefore, if the grade table is used, it is possible to determine univocally, from contents of dirt components in a lacrimal fluid of a wearer, a degree of suitability of the combination of contact lens C and care system CS-1 for the wearer.

In addition, with respect to other combinations than the combination of contact lens C and care system CS1, that is, a combination of contact lens A and care system CS-1, a combination of contact lens B and care system CS-1, a combination of contact lens D and care system CS-1, a combination of contact lens A and care system CS-2, and so on, similar grade tables are obtained. Thus, a data base for selecting, from the contact-lens group and the care-system group shown in FIG. 1, a contact lens suitable for a wearer and/or a care system therefor is obtained.

When a contact lens suitable for a wearer (a purchaser) and a care system therefor are selected using the thus obtained data base, first, a lacrimal-fluid examination is carried out on the wearer so as to detect a protein content ($P^0$) and a lipid content ($L^0$) of a lacrimal fluid of the wearer, as described above. Then, the detected protein content ($P^0$) and/or the detected lipid content ($L^0$) are or is checked against each of the respective grade tables corresponding all the combinations of contact lens and care system, so as to determine a degree of suitability of each of the combinations for the wearer. Thus, one or more combinations of contact lens and care system suitable for the wearer can be selected from all the combinations. For example, if the protein content and lipid content of the lacrimal fluid of the wearer are 8.0 μg and 0.6 μg, respectively, TABLE 5 as the grade table corresponding to the combination of contact lens C and care system CS-1 indicates that wearing of lens C is suitable ("○"). Thus, the combination of contact lens C and care system CS-1 is selected as one combination of contact lens and care system suitable for the wearer.

Since the data base is used as the criteria, a contact lens suitable for a wearer and/or a care system therefor can be more reliably and easily selected based on amounts of dirt components in a lacrimal fluid of the wearer (the purchaser). Thus, various problems that may adversely influence the eye of the wearer, such as worsening in the feel during wearing, lowering in the oxygen permeability of the lens, shortening in the lens life, lowering in the visual acuity, or injury of the cornea, can be effectively prevented or avoided.

<2. Method of Determining Criteria Based on Dirt Adhesion Amounts>

Like the above-described <1. Method of Determining Criteria Based on Dirt Adhesion Amounts and Clinical Examination Results>, first, one contact lens is selected from a plurality of sorts of contact lenses and one care system is selected from a plurality of sorts of care systems, and the selected contact lens and the selected care system are combined (again, the combination of contact lens C and care system CS-1 is used). Second, a wearing test in which a plurality of arbitrary subjects ($Y_1, \ldots, Y_n$) each wear contact lens C, and care lens C with care system CS-1, for a predetermined period (12 weeks), is carried out. After the wearing test, respective amounts ($P^{12}_1, \ldots, P^{12}_n$) of protein adhered and deposited to and on contact lenses C, and respective amounts ($L^{12}_1, \ldots, L^{12}_n$) of lipid adhered and deposited to and on lenses C are detected.

Then, a mean and a standard deviation (σ) of the respective detected protein adhesion amounts ($P^{12}_1, \ldots, P^{12}_n$) of the subjects ($Y_1, \ldots, Y_n$) and a mean and a standard deviation (σ) of the respective detected lipid adhesion amounts ($L^{12}_1, \ldots, L^{12}_n$) of the subjects are determined, and the thus obtained means and standard deviations are used to divide the respective distributions of the respective detected protein adhesion amounts of the subjects and the respective detected lipid adhesion amounts of the same, into a plurality of classes, and thereby determine a degree of suitability of the combination of contact lens C and care system CS-1 with respect to each of the classes. Here, evaluation criteria shown in TABLE 6 are employed, and degrees of suitability shown in TABLE 7 are obtained. In the present embodiment, the respective means and standard deviations of the dirt adhesion amounts were determined as follows:

protein dirt: 3.4±0.7 (σ)

lipid dirt: 2.4±0.6 (σ)

TABLE 6

| SYMBOLS | DIRT ADHESION AMOUNTS | SUITABILITY |
|---------|----------------------|-------------|
| ◎ | <(MEAN − σ) | WEARING IS FULLY GOOD |
| ○ | (MEAN − σ) TO (MEAN + σ) | WEARING IS GOOD |
| ▲ | (MEAN + σ) TO (MEAN + 2σ) | WEARING NEEDS CARE |
| ● | >(MEAN + 2σ) | WEARING IS NOT RECOMMENDED |

TABLE 7

| | | $L^{12}$ [μg] | | | |
|---|---|---|---|---|---|
| | | 0~1.8 | 1.8~3.0 | 3.0~3.6 | >3.6 |
| $P^{12}$ [μg] | 0~2.7 | ◎ | ○ | ▲ | ● |
| | 2.7~4.1 | ○ | ○ | ▲ | ● |
| | 4.1~4.8 | ▲ | ▲ | ▲ | ● |
| | >4.8 | ● | ● | ● | ● |

◎: WEARING IS FULLY GOOD
○: WEARING IS GOOD
▲: WEARING NEEDS CARE
●: WEARING IS NOT RECOMMENDED

The degrees of suitability shown in TABLE 7 correspond to those shown in TABLE 3 obtained in <1. Method of Determining Criteria Based on Dirt Adhesion Amounts and Clinical Examination Results>. Therefore, like TABLE 3, it is difficult to use TABLE 7 as it is, to obtain criteria for estimating a dirt adhesion characteristic with respect to contact lens C, or selecting a contact lens and/or a care system according to the present invention. Hence, like the above-described method, a lacrimal-fluid analysis is carried out on the subjects, and a relationship between dirt adhesion amounts ($P^{12}$, $L^{12}$) detected in the wearing test and respective contents ($P^0$, $L^0$) of dirt components detected in the lacrimal-fluid analysis, is obtained by a known analyzing method such as least square method. Thus, it is possible to estimate, from the respective contents ($P^0$, $L^0$) of dirt components detected in the lacrimal-fluid analysis, dirt amounts that would be adhered to contact lens C if a wearer would use lens C and care system CS-1, i.e., a dirt adhesion characteristic of the wearer with respect to lens C, and eventually determine univocally a degree of suitability of lens C and care system CS-1 for the wearer. In addition, the obtained relationship (the expressions similar to the above-indicated Expressions 1 and 2) is used to convert TABLE 7 (grade table) into TABLE 8, by converting the dirt adhesion amounts ($P^{12}$, $L^{12}$) detected in the wearing test into the respective contents ($P^0$, $L^0$) of protein and lipid detected in the lacrimal-fluid analysis.

Like the grade table (TABLE 5), the thus obtained grade table (TABLE 8) can be advantageously used as criteria for determining a degree of suitability of the combination of contact lens C and care system CS-1 for a wearer. In addition, with respect to other combinations than the combination of contact lens C and care system CS1 (that is, a combination of contact lens A and care system CS-1, a combination of contact lens B and care system CS-1, a combination of contact lens D and care system CS-1, a combination of contact lens A and care system CS-2, and so on), similar grade tables are obtained. Thus, a data base for selecting, from the contact-lens group and the care-system group shown in FIG. 1, a contact lens suitable for a wearer and/or a care system therefor is obtained. Therefore, like the above-described method, one or more combinations of contact lens and care system suitable for a wearer (a purchaser) can be more reliably and easily selected, and various problems that may adversely influence the eye of the wearer, such as worsening in the feel during wearing, lowering in the oxygen permeability of the lens, shortening in the lens life, lowering in the visual acuity, or injury of the cornea, can be effectively prevented or avoided.

TABLE 8

| | | $L^0$ [µg] | | | |
|---|---|---|---|---|---|
| | | 0~0.34 | 0.34~0.55 | 0.55~0.65 | >0.65 |
| $P^0$ [µg] | 0~4.26 | ⊚ | ○ | ▲ | ● |
| | 4.26~5.75 | ○ | ○ | ▲ | ● |
| | 5.75~6.49 | ▲ | ▲ | ▲ | ● |
| | >6.49 | ● | ● | ● | ● |

⊚: WEARING IS FULLY GOOD
○: WEARING IS GOOD
▲: WEARING NEEDS CARE
●: WEARING IS NOT RECOMMENDED

The foregoing description relates to concrete methods of determining criteria for estimating, from contents of dirt components in a lacrimal fluid of a wearer, dirt adhesion characteristics of the wearer with respect to contact lenses and selecting a contact lens suitable for the wearer and/or a care system therefor, that is, methods of producing a data base used for the same purpose. However, the above-described two methods are just examples according to the present invention, and the present invention is by no means limited to the details of those examples.

Meanwhile, the above-described criteria are obtained based on the results of the wearing test and the lacrimal-fluid analysis that are carried on the arbitrary subjects. Therefore, the greater the total number, n, of the subjects is, the more reliable the criteria are, i.e., the more accurate the selection is. Thus, it is desirable to carry out, with respect to the wearers (the purchasers) who have undergone the above-described lacrimal-fluid analysis in which the contents ($P^0$, $L^0$) of dirts that adhere to a contact lens used in the lacrimal-fluid analysis are detected, a follow-up study in which a protein content and/or a lipid content with respect to the combination of contact lens and care system that is used by each wearer are or is detected, and/or whether ophthalmologic problems (feeling of wearing, drying, congestion, cornea stain, etc.) have occurred to each wearer is judged, so that the results of the follow-up study are accumulated in the data base.

Figure 4:
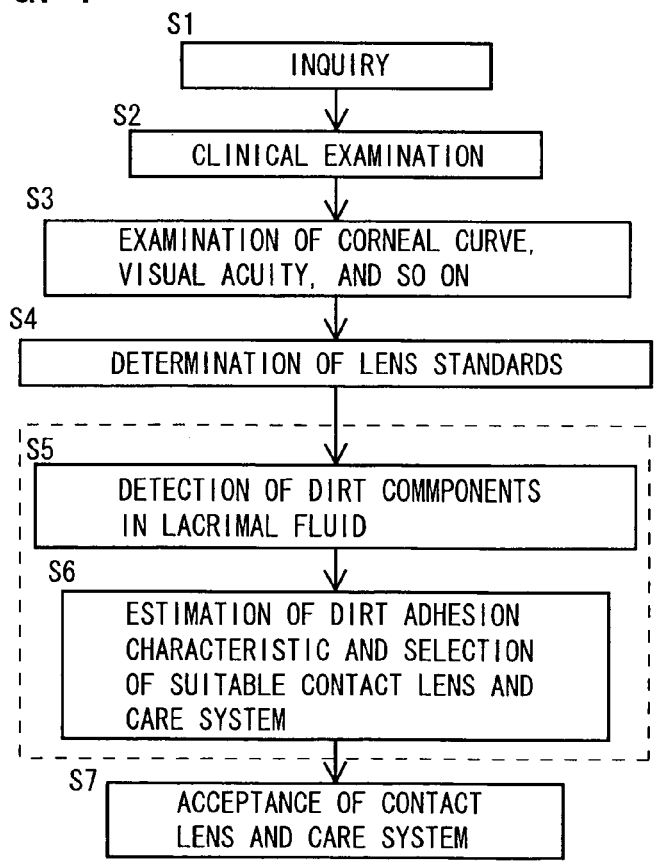
FIG. 4 is a flow chart representing a representative example of a method of selecting a contact lens and a care system therefor, according to the present invention.

Finally, a series of steps that are taken, by a wearer who wishes to purchase a contact lens according to the above-described selecting method, for the purpose of actually determining the lens, will be described below by reference to a flow chart shown in FIG. 4.

First, a wearer is inquired about what kinds of eye diseases or other diseases the wearer has suffered in the lifetime (Step S1). Then, the wearer is clinically examined about whether the anterior eye (e.g., cornea or anterior sac) or the external eye (e.g., conjunctiva or eyelid) does not have injury or inflammation, whether the position of the crystalline lens is normal, whether the crystalline lens is not turbid, whether the eyeground is normal, whether the amount of lacrimal fluid is appropriate, and so on (Step S2). If there are no problems that cannot allow the wearer to wear a contact lens, then a corneal curve, a visual acuity, etc. of the wearer are measured for the purpose of selecting a contact lens that fits the eye of the wearer and ensures that the wearer enjoys a good visual acuity (Step S3). Thus, contact-lens standards, such as a base curve, a diameter, a diopter, etc., that are suitable for the eye of the wearer are determined (Step S4).

Next, according to the present invention, a lacrimal fluid of the wearer is collected, and respective contents of dirt components in the lacrimal fluid are detected (Step S5). In addition, based on the detected contents of the dirt components, dirt adhesion characteristics of the wearer with respect to contact lenses are estimated, and one or more combinations of contact lens and care system suitable for the wearer is or are selected (Step S6).

Then, the wearer chooses, from the thus selected combination or combinations of contact lens and care system, an appropriate combination of contact lens and care system, and actually wears the contact lens so as to feel the lens and see with the lens. In addition, the wearer who is wearing the contact lens is clinically examined about the fitting of the lens and the visual acuity of the eye. If there are no problems, the chosen contact lens and the care system therefor are accepted (Step S7).

While the present invention has been described in its preferred embodiments, it is to be understood that the present invention is by no means limited to the details of the described embodiments but may otherwise be embodied.

For example, in each of the illustrated embodiments, the protein content and the lipid content are both detected. However, it is possible to employ a manner in which only one of the protein content and the lipid content is detected, or a manner in which a content of the sum of protein and lipid is detected.

In each of the illustrated embodiments, the above-described data base is advantageously used in selecting, based on the respective detected contents ($P^0$, $L^0$) of protein and lipid, the contact lens suitable for the wear and/or the care system therefor. To this end, a data processing device such as a computer may be advantageously used to construct the data base or extract, from the data base, one or more suitable combinations of contact lens and care system.

According to the present invention, a care system may comprise not only one or more lens care products but also a proposal of a method of using the lens care product or products. For example, the above-described care system CS-2 that is constituted by a solution set obtained by combining a single solution that can clean, rinse, sterilize and preserve a contact lens, and a protein removing solution with each other, may be further classified by a proposal of a method of using the solution set. For example, for a wearer who is estimated to suffer too large an amount of adhesion of protein dirt, a method of using the solution set such that the protein removing solution is used every day, may be proposed; and for a wearer who is estimated to show only a small amount of adhesion of protein dirt, a different method of using the solution set such that the protein removing solution is used once a week, may be proposed.

In each of the illustrated embodiments, after the clinical examination (Step S2), etc, the amounts of dirt components in the lacrimal fluid are independently detected (Step S5). However, it is possible to detect, when an amount of lacrimal fluid is measured to diagnose, e.g., dry eye disease, amounts of dirt components present in the lacrimal fluid. If the contents of dirt components in the lacrimal fluid are detected simultaneously with the measurement of amount of the lacrimal fluid, the total number of examination items is reduced.

In addition, in each of the illustrated embodiments, the contents of protein and lipid in the lacrimal fluid of the wearer are measured and expressed in digits. However, in the case where the coloring reagents are used, the content of each of the protein and the lipid can be recognized by a color tone. Therefore, it is possible to prepare, beforehand, color-tone specimens, and determine a content of each of the protein and the lipid by comparing the developed color with those color-tone specimens, so that based on the thus determined contents of protein and lipid, dirt adhesion characteristics of the wearer with respect to contact lenses are estimated and a contact lens suitable for the wearer and/or a care system therefor are selected.

It is to be understood that the present invention may be embodied with various changes, modifications, and improvements that may occur to a person skilled in the art, though those embodiments are not described any more, and that those embodiments fall within the scope of the present invention, without departing from the spirit thereof.

As is apparent from the foregoing description, the contact lens and care system selecting method in accordance with the present invention includes carrying out the lacrimal-fluid analysis, estimating, based on the results of the analysis, the dirt adhesion characteristics with respect to the contact lenses, and selecting the contact lens and/or the care system therefor. Therefore, the occurrence of the problems that may be caused by the dirt adhered and deposited to and on the contact lens, such as worsening in the feel during wearing, lowering in the oxygen permeability of the lens, shortening in the lens life, lowering in the visual acuity, or injury of the cornea, can be effectively avoided, and accordingly the high safety for the eye of the wearer can be ensured.

What is claimed is:

1. A method of selecting at least one of a contact lens and a care system, the method comprising the steps of
    detecting at least one of a protein content and a lipid content in a lacrimal fluid of a wearer who is to wear a contact lens,
    estimating, based on the detected at least one of the protein content and the lipid content, a dirt adhesion characteristic of the wearer with respect to a contact lens, and
    selecting, based on the estimated dirt adhesion characteristic, at least one of a contact lens suitable for the wearer and a care system therefor, from at least one of (a) a plurality of contact lenses and (b) a plurality of care systems.

2. The method according to claim 1, wherein the step of detecting said at least one of the protein content and the lipid content comprises causing the lacrimal fluid to contact a coloring reagent.

3. The method according to claim 2, wherein the step of detecting comprises collecting, with a lacrimal-fluid collecting medium, the lacrimal fluid of the wearer, and causing the collected lacrimal fluid to contact the coloring reagent.

4. The method according to claim 3, wherein the step of detecting comprises using, as the lacrimal-fluid collecting medium, a medium selected from the group consisting of a thread, a paper, a tube, a polymer film, and a sponge.

5. The method according to claim 2, wherein the step of detecting comprises causing, in advance, a lacrimal-fluid collecting medium to contain the coloring reagent, collecting, with the lacrimal-fluid collecting medium containing the coloring reagent, the lacrimal fluid of the wearer, and causing the collected lacrimal fluid to contact the coloring reagent contained by the lacrimal-fluid collecting medium.

6. The method according to claim 2, wherein the step of detecting the protein content comprises using, as the, coloring reagent, at least one reagent selected from the group consisting of Bromochlorophenol Blue, Bromophenol Blue, Bromocresol Purple, and Tetrabromophenol Blue.

7. The method according to claim 1, wherein the step of detecting said at least one of the protein content and the lipid content comprises carrying out an analysis selected from the group consisting of a colorimetric analysis, a spectral analysis, a fluorometric analysis, and an analysis obtained by combining two or more of those analyses.

* * * * *